United States Patent
Walsdorff et al.

(10) Patent No.: US 7,285,685 B2
(45) Date of Patent: Oct. 23, 2007

(54) METHOD FOR DEHYDROGENATION OF CARBONYL COMPOUNDS

(75) Inventors: Christian Walsdorff, Ludwigshafen (DE); Beatrice Rössler, Bad Dürkheim (DE); Götz-Peter Schindler, Mannheim (DE); Joaquim H. Teles, Otterstadt (DE); Klaus Harth, Altleiningen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/565,730

(22) PCT Filed: Jul. 22, 2004

(86) PCT No.: PCT/EP2004/008191

§ 371 (c)(1),
(2), (4) Date: Oct. 12, 2006

(87) PCT Pub. No.: WO2005/009937

PCT Pub. Date: Feb. 3, 2005

(65) Prior Publication Data

US 2007/0032681 A1 Feb. 8, 2007

(30) Foreign Application Priority Data

Jul. 24, 2003 (DE) ................. 103 33 755

(51) Int. Cl.
*C07C 45/65* (2006.01)

(52) U.S. Cl. .................... 568/343; 568/388; 568/398; 568/446; 568/459

(58) Field of Classification Search .................... None
See application file for complete search history.

(56) References Cited

U.S. PATENT DOCUMENTS 5,087,792 A * 2/1992 Cottrell et al. .............. 585/661
5,389,342 A * 2/1995 Savage et al. .............. 422/109
6,433,229 B1 8/2002 Fischer et al.

FOREIGN PATENT DOCUMENTS

| DE | 19911169 A1 | 3/1999 |
| JP | 49-127909 A2 | 12/1974 |
| WO | WO-00/55108 A1 | 9/2000 |

* cited by examiner

Primary Examiner—Sikarl A. Witherspoon
(74) Attorney, Agent, or Firm—Connolly Bove Lodge and Hutz

(57) ABSTRACT

Process for preparing alpha, beta-unsaturated acyclic or cyclic carbonyl compounds by dehydrogenation of the corresponding saturated carbonyl compounds in the gas phase over a heterogeneous dehydrogenation catalyst comprising platinum and/or palladium and tin on an oxidic support.

20 Claims, 1 Drawing Sheet

METHOD FOR DEHYDROGENATION OF CARBONYL COMPOUNDS

This application is a National Stage of PCT/EP2004/008191 filed Jul. 22, 2004 which in turn claims priority from German Application 103 33 755.5, filed Jul. 24, 2003.

The invention relates to a process for preparing alpha, beta-unsaturated acyclic or cyclic carbonyl compounds by dehydrogenation of the corresponding saturated carbonyl compounds in the gas phase over a heterogeneous dehydrogenation catalyst.

JP 49127909 A2 describes a process for the dehydrogenation of saturated ketones. In this process, butanone can be converted at 500° C. over a catalyst comprising iron oxide, aluminum oxide and potassium oxide with addition of water vapor into 1-buten-3-one at a conversion of 5.5% and a selectivity of 83%.

However, such catalysts based on iron oxide have to be used with a relatively large amount of water vapor in relation to the hydrocarbon to be dehydrogenated and nevertheless deactivate very quickly in the presence of hydrocarbons having oxo functions.

U.S. Pat. No. 6,433,229 B1 describes a process for preparing cyclic alpha, beta-unsaturated ketones by dehydrogenation of the corresponding saturated ketones, in particular the dehydrogenation of cyclopentanone to 2-cyclopenten-1-one, in the gas phase over heterogeneous catalysts in the presence of less than 0.1 mol of oxygen per mole of the starting material to be dehydrogenated. Catalysts described are CuO, AgO, PdO, NiO, $Mn_2O_3$ or $Re_2O_7$ on ZnO, CaO, BaO, $SiO_2$ or $Al_2O_3$. In an example, a catalyst comprising 9.5% of Pd and 0.55% of Pt on $ZrO_2$ is used. According to the description, the regeneration of the catalysts takes place at from 400 to 500° C.

The catalysts described in U.S. Pat. No. 6,433,229 B1, too, are deactivated within hours under the conditions described there. In addition, regeneration at from 400 to 500° C. is not very practical from a reaction engineering point of view, since a very large degree of dilution of the oxygen-containing gas with inert gas is necessary to avoid relatively high hot spot temperatures, and this makes regeneration time-consuming, cumbersome and expensive. Furthermore, temperatures in the range from 400 to 500° C. are generally not sufficient to remove carbon-containing deposits completely from the catalysts, in particular from deep-down pore systems, within practicable regeneration times. On the other hand, relatively high hot spot temperatures can lead to damage to the catalysts described, for example due to sintering of the oxidic materials.

It is an object of the present invention to find an improved process for the dehydrogenation of hydrocarbons containing oxo functions in the gas phase over heterogeneous catalysts. This should also include, in particular, simple and practicable regeneration on the catalysts.

We have found that this object is achieved by a process for preparing alpha, beta-unsaturated acyclic or cyclic carbonyl compounds by dehydrogenation of the corresponding saturated carbonyl compounds in the gas phase over a heterogeneous dehydrogenation catalyst comprising platinum and/or palladium and tin on an oxidic support.

The dehydrogenation catalysts used according to the present invention generally comprise a support and an active composition. The support comprises a heat-resistant oxide or mixed oxide. The support present in the dehydrogenation catalyst is preferably a metal oxide selected from the group consisting of zirconium dioxide, zinc oxide, aluminum oxide, silicon dioxide, titanium dioxide, magnesium oxide, lanthanum oxide, cerium oxide and mixtures thereof. Preferred supports are zirconium dioxide and/or silicon dioxide, particularly preferably mixtures of zirconium dioxide and silicon dioxide.

The active composition of the dehydrogenation catalyst used according to the present invention comprises platinum and/or palladium as active metals. In addition, the dehydrogenation catalyst further comprises tin. In general, the dehydrogenation catalyst contains from 0.01 to 2% by weight, preferably from 0.1 to 1% by weight, particularly preferably from 0.2 to 0.6% by weight, of palladium and/or platinum and from 0.01 to 10% by weight, preferably from 0.2 to 2% by weight, particularly preferably from 0.4 to 1% by weight, of tin, based on the total weight of the dehydrogenation catalyst. If platinum is present as active metal in the dehydrogenation catalyst, the weight ratio of platinum:tin is preferably from 1 to 3, in particular about 2.

In addition, the dehydrogenation catalyst can further comprise one or more elements of main group I and/or II, preferably potassium and/or cesium. Furthermore, the dehydrogenation catalyst can comprise one or more elements of transition group III including the lanthanides and actinides, preferably lanthanum and/or cerium. Finally, the dehydrogenation catalyst can further comprise one or more elements of main group III and/or further elements of main group IV, preferably one or more elements from the group consisting of boron, gallium, silicon and lead.

In a preferred embodiment, the dehydrogenation catalyst comprises palladium and/or platinum and tin and in addition at least one element of main group I and/or II and at least one element of transition group III including the lanthanides and actinides.

In advantageous embodiments, the active composition contains the following further components:

at least one element of main group I or II, preferably cesium and/or potassium, in an amount of from 0 to 20% by weight, preferably from 0.1 to 10% by weight, particularly preferably from 0.2 to 1.0% by weight, based on the total weight of the catalyst;

at least one element of transition group III including the lanthanides and actinides, preferably lanthanum and/or cerium, in an amount of from 0 to 20% by weight, preferably from 0.1 to 15% by weight, particularly preferably from 0.2 to 10% by weight, in particular from 1 to 5% by weight, based on the total weight of the catalyst.

The dehydrogenation catalyst is preferably halogen-free.

Preparation of the Dehydrogenation Catalyst

To prepare the dehydrogenation catalysts used according to the present invention, it is possible to use precursors of oxides of zirconium, silicon, aluminum, titanium, magnesium, lanthanum or cerium which can be converted into the oxides by calcination. These can be prepared by known methods, for example by the sol-gel process, precipitation of salts, dehydration of the corresponding acids, dry mixing, slurrying or spray drying. For example, to prepare a $ZrO_2.Al_2O_3.SiO_2$ mixed oxide, a water-rich zirconium oxide of the formula $ZrO_2.xH_2O$ can firstly be prepared by precipitation of a suitable zirconium-containing precursor. Suitable zirconium precursors are, for example, $Zr(NO_3)_4$, $ZrOCl_2$ or $ZrCl_4$. The precipitation itself is carried out by addition of a base such as NaOH, KOH, $Na_2CO_3$ and $NH_3$ and is described, for example, in EP-A 0 849 224.

To prepare a $ZrO_2.SiO_2$ mixed oxide, the zirconium-containing precursor obtained as described above can be mixed with a silicon-containing precursor. Well-suited precursors for $SiO_2$ are, for example, water-containing sols of $SiO_2$, e.g. Ludox™. Mixing of the two components can be carried out, for example, by simple mechanical mixing or by spray drying in a spray drier.

To prepare a $ZrO_2.SiO_2.Al_2O_3$ mixed oxide, the $SiO_2.ZrO_2$ powder mixture obtained as described above can be admixed with an aluminum-containing precursor. This can be achieved, for example, by simple mechanical mixing in a kneader. However, a $ZrO_2.SiO_2.Al_2O_3$ mixed oxide can also be prepared in a single step by dry mixing the individual precursors.

The supports for the dehydrogenation catalysts used according to the present invention have, inter alia, the advantage that they can easily be shaped. For this purpose, the powder mixture obtained is admixed with a concentrated acid in a kneader and then converted into a shaped body, e.g. by means of a ram extruder or a screw extruder.

In particular embodiments, the dehydrogenation catalysts used according to the present invention have a defined pore structure. When mixed oxides are used, there is the opportunity of influencing the pore structure in a targeted manner. The particle sizes of the various precursors influence the pore structure. Thus, for example, the use of $Al_2O_3$ having a low loss on ignition and a defined particle size distribution enables macropores to be generated in the microstructure. In this context, the use of $Al_2O_3$ having a loss on ignition of about 3% (e.g. Puralox®) has been found to be useful.

A further possible way of preparing a support having a specific pore radius distribution for the dehydrogenation catalysts used according to the present invention is to add various polymers during preparation of the support. These are then partly or completely removed by calcination to produce pores in defined pore radius ranges. Mixing of the polymers and the oxide precursors can, for example, be carried out by simple mechanical mixing or by spray drying in a spray drier.

The use of PVP (polyvinylpyrrolidone) has been found to be particularly useful for preparing supports having a bimodal pore radius distribution. If this is added in a preparation step to one or more oxide precursors for oxides of the elements Zr, Ti, Al or Si, macropores in the range from 200 to 5000 nm are formed after calcination. A further advantage of the use of PVP is the ready shapeability of the support. Thus, extrudates having good mechanical properties can be produced easily from freshly precipitated water-containing $ZrO_2.x\,H_2O$ which has previously been dried at 120° C. with addition of PVP and formic acid even without further oxide precursors.

The calcination of the supports for the dehydrogenation catalysts used according to the present invention is advantageously carried out after application of the active components and is carried out at from 400 to 1000° C., preferably from 500 to 700° C., particularly preferably from 550 to 650° C. and in particular at from 560 to 620° C. The calcination temperature should usually be at least as high as the reaction temperature in the dehydrogenation in which the dehydrogenation catalysts according to the present invention are used.

The supports for the dehydrogenation catalysts used according to the present invention generally have high BET surface areas after calcination. The BET surface area is generally greater than 40 $m^2/g$, preferably greater than 50 $m^2/g$, particularly preferably greater than 70 $m^2/g$. The pore volume of the dehydrogenation catalysts according to the present invention is usually from 0.2 to 0.6 ml/g, preferably from 0.25 to 0.5 ml/g. The mean pore diameter of the dehydrogenation catalysts according to the present invention determined by Hg porosimetry is from 3 to 20 nm, preferably from 4 to 15 nm.

A further characteristic of the dehydrogenation catalysts used according to the present invention is a bimodal pore radius distribution. The pores are in the ranges up to 20 nm and from 40 to 5000 nm. These pores make up a total of at least 70% of the total pore volume of the dehydrogenation catalyst. The proportion of pores smaller than 20 nm is generally in the range from 20 to 60%, while the proportion of pores in the range from 40 to 5000 nm is generally likewise in the range from 20 to 60%.

The dehydrogenation-active component is generally applied by impregnation with a suitable metal salt precursor. Instead of impregnation with a suitable metal salt precursor, the dehydrogenation-active component can also be applied by other methods such as spraying the metal salt precursor onto the support. Suitable metal precursors are, for example, the nitrates, acetates and chlorides of the appropriate metals, and complex anions of the metals used are also possible. Preference is given to using platinum as $H_2PtCl_6$, platinum (II) oxalate or $Pt(NO_3)_2$ and palladium is preferably used as palladium(II) oxalate or $Pd(NO_3)_2$. Both water and organic solvents are suitable solvents for the metal salt precursors. Particularly useful solvents are water and lower alcohols such as methanol and ethanol.

Further suitable precursors when using noble metals as dehydrogenation-active components are the corresponding noble metal sols which can be prepared by one of the known methods, for example by reduction of a metal salt by means of a reducing agent in the presence of a stabilizer such as PVP. The technique is comprehensively described in the German patent application DE 195 00 366.

The further components of the active composition can be applied either during the preparation of the support, for example by coprecipitation, or subsequently, for example by impregnating the support with suitable precursor compounds. As precursor compounds, use is generally made of compounds which can be converted into the corresponding oxides by calcination. Examples of suitable precursors are hydroxides, carbonates, oxalates, acetates, chlorides or mixed hydroxycarbonates of the appropriate metals.

To apply alkali metals and alkaline earth metals, it is advantageous to use aqueous solutions of compounds which can be converted into the corresponding oxides by calcination. Examples of suitable compounds are hydroxides, carbonates, oxalates, acetates or basic carbonates of the alkali metals and alkaline earth metals. If the catalyst support is doped with metals of main or transition group III, use is frequently made of the hydroxides, carbonates, nitrates, acetates, formates or oxalates which can be converted into the corresponding oxides by calcinations, for example $La(OH)_3$, $La_2(CO_3)_2$, $La(NO_3)_3$, lanthanum acetate, lanthanum formate or lanthanum oxalate.

The dehydrogenation catalyst can be present in the reactor as a fixed bed or, for example, in the form of a fluidized bed and can have an appropriate shape. Suitable shapes are, for example, granules, pellets, monoliths, spheres, or extrudates (rods, wagon wheels, stars, rings).

Preparation of a Preferred Catalyst Support

In a particularly preferred embodiment of the process of the present invention, use is made of a catalyst support which is obtainable by mixing zirconium dioxide powder with a monomeric, oligomeric or polymeric organosilicon compound as binder, if desired a pore former, if desired an acid, water and, if desired, further additives to produce a kneadable composition, the composition is homogenized, shaped to produce shaped bodies, dried and calcined.

Mixing essentially monoclinic zirconium dioxide powder having a high surface area with an organosilicon compound which forms $SiO_2$ on calcination as binder, shaping to produce shaped bodies such as pellets, extrudates and spheres and calcining the shaped bodies makes it possible to produce catalyst supports having a high mechanical stability and a pore structure which is very suitable for the dehydrogenation of carbonyl compounds, The catalyst supports obtained are sufficiently stable to withstand several hundred oxidative regeneration cycles without mechanical damage or loss of activity.

The organosilicon compounds used as binders are generally liquid. In this way, the high surface areas zirconium dioxide is uniformly wetted with the organosilicon compound during mixing, as a result of which the zirconium dioxide particles are surrounded and partly impregnated by the organosilicon compound. This results in a high bond strength between the zirconium dioxide particles and very good mechanical stability of the shaped catalyst support bodies obtained. On calcination of the shaped catalyst support bodies, the organic radicals of the organosilicon binder are burnt. This forms $SiO_2$ which is very finely dispersed in the zirconium dioxide matrix. Combustion of the organic radicals of the organosilicon binder forms additional pores. These pores are, owing to the uniform distribution of the organosilicon binder in the zirconium dioxide matrix, likewise very uniformly distributed. This increases the total porosity of the catalyst support. In addition, the presence of $SiO_2$ effects stabilization of the zirconium dioxide against thermal sintering. This effect becomes increasingly pronounced, the more uniformly the silicon dioxide is distributed.

Suitable organosilicon binders are monomeric, oligomeric or polymeric silanes, alkoxysilanes, aryloxysilanes, acyloxysilanes, oximinosilanes, halosilanes, aminoxysilanes, aminosilanes, amidosilanes, silazanes or silicones, as are described, for example, in Ullmann's Encyclopedia of Industrial Chemistry, Vol. A24, on pages 21 to 56. These include, in particular, the monomeric compounds of the formulae (I) to (VI):

   (Hal)$_x$SiR$_{4-x}$ (I)

   (Hal)$_x$Si(OR$^1$)$_{4-x}$ (II)

   (Hal)$_x$Si(NR$^1$R$^2$)$_{4-x}$ (III)

   R$_x$Si(OR$^1$)$_{4-x}$ (IV)

   R$_x$Si(NR$^1$R$^2$)$_{4-x}$ (V)

   (R$^1$O)$_x$Si(NR$^1$R$^2$)$_{4-x}$ (VI)

where
Hal are each, independently of one another, a halogen (F, Cl, Br or I),
R are each, independently of one another, H or a substituted or unsubstituted alkyl, alkenyl, alkynyl, cycloalkyl, cycloalkenyl, arylalkyl or aryl radical,
$R^1$, $R^2$ are each, independently of one another, H or a substituted or unsubstituted alkyl, acyl, arylalkyl or aryl radical, and
x is from 0 to 4.

R, $R^1$ and $R^2$ can each be H or an alkyl radical, preferably a $C_1$-$C_6$-alkyl radical, which may be linear or branched. If R is an alkyl radical, R is particularly preferably methyl, ethyl, n-propyl, isopropyl, n-butyl, sec-butyl or tert-butyl, especially methyl or ethyl. R, $R^1$ and $R^2$ can each also be an aryl radical, preferably phenyl, or an arylalkyl radical, preferably benzyl.

Furthermore, R can also be an alkenyl radical, preferably a $C_2$-$C_6$-alkenyl radical, in particular vinyl or allyl, or an alkynyl radical, preferably ethynyl.

Furthermore, $R^1$ and $R^2$ may each also be an acyl radical, preferably a $C_2$-$C_6$-acyl radical, in particular an acetyl radical.

Examples of suitable organosilicon compounds of the formula (I) are $SiCl_4$, $MeSiCl_3$, $Me_2SiCl_2$ and $Me_3SiCl$.

Suitable organosilicon compounds of the formula (IV) are, for example, $Si(OEt)_4$, $MeSi(OEt)_3$, $Me_2Si(OEt)_2$ and $Me_3SiOEt$.

Suitable compounds of the formula (V) are, for example, $Me_3Si(NMeCOMe)$ and $MeSi(NMeCOCH_2C_6H_5)$.

An example of a suitable compound of the formula (VI) is $(MeO)_3SiNMe_2$.

Examples of suitable oligomeric and polymeric organosilicon compounds are methylsilicones and ethylsilicones.

Very particularly preferred organosilicon binders are methylsilicones, for example the Silres® grades from Wacker.

In a first step, zirconium dioxide powder is mixed with the organosilicon binder, if desired a pore former, if desired an acid, water and, if desired, further additives to produce a kneadable composition. Preference is given to mixing
a) from 50 to 98% by weight of zirconium dioxide powder,
b) from 2 to 50% by weight, particularly preferably from 5 to 20% by weight, of the organosilicon compound,
c) from 0 to 48% by weight, particularly preferably from 0 to 10% by weight, of pore former, and
d) from 0 to 48% by weight, particularly preferably from 0 to 10% by weight, of further additives, where the sum of the components a) to d) is 100% by weight, with addition of water and an acid to give a kneadable composition.

The zirconium dioxide powder has a high surface area and is usually substantially monoclinic zirconium dioxide powder. Substantially monoclinic zirconium dioxide powder, comprising from 85 to 100% by weight, preferably from 90 to 100% by weight, of monoclinic zirconium dioxide can be prepared as described in EP-A 0 716 883 by precipitation of zirconium salts with ammonia, by adding a zirconyl nitrate or zirconyl chloride solution to an aqueous ammonia solution so that the pH drops from 14 to 6, washing the precipitation product and drying and calcining it. For this purpose, a concentrated, generally from 2 to 5 mol % strength, zirconium chloride solution is firstly prepared from zirconium carbonate and hydrochloric acid or, preferably, a concentrated, generally from 2 to 5 mol % strength, zirconium nitrate solution is firstly prepared from zirconium carbonate and nitric acid. This solution is added to an initially charged aqueous ammonia solution (about 15 mol % of $NH_3$), generally at from 20 to 60° C., with monitoring of the pH. The addition is stopped at a pH of 6-8 and the pH must not drop below 6. This is followed by a further stirring time of generally from 30 to 600 minutes.

The precipitation product is washed and substantially freed of ammonium salts, for example on a filter press, dried and calcined in air at from 300 to 600° C., preferably from 400 to 500° C., and a pressure of from 0.05 to 1 bar. The substantially monoclinic zirconium dioxide prepared in this way occasionally contains small amounts of tetragonal or cubic modification. The proportion of tetragonal or cubic modification can be reduced down to the X-ray detection limit by carrying out drying under a partial pressure of water vapor of from 0.2 to 0.9 bar prior to the calcination. This drying takes, for example, about 16 hours at 120° C.

Water is usually added to the zirconium dioxide powder and the organosilicon compound in order to obtain a kneadable composition.

Furthermore, an acid can be added to the catalyst support composition. This effects peptization of the kneadable composition. Suitable acids are, for example, nitric acid and acetic acid, preferably nitric acid.

The catalyst support composition usually further comprises a pore former. Suitable pore formers are, for example, polyalkylene oxides such as polyethylene oxide, carbohydrates such as cellulose and sugar, natural fibers, pulp or synthetic polymers such as polyvinyl alcohol.

The catalyst support molding composition can further comprise additional additives. Further additives are, for example, known compounds which influence the rheology.

The components a) to f) are mixed and homogenized in customary mixing apparatuses. Suitable mixing apparatuses are, for example, kneaders, pan mills and Mix-Mullers which ensure good mixing and homogenization of the initially inhomogeneous kneadable composition. The catalyst support molding composition is subsequently shaped to give shaped bodies, for example by extrusion to produce extrudates or hollow supports.

The shaped catalyst support bodies are then usually dried. Drying is carried out, for example, at from 90 to 120° C. for a period of from 10 to 100 hours.

The dried shaped catalyst support body is subsequently calcined. Calcination is usually carried out at from 300 to 800° C., preferably from 400 to 600° C., for a period of from 0.5 to 6 hours. Calcination is preferably carried out in air and at atmospheric pressure.

Calcination of the catalyst supports impregnated with the appropriate metal salt solutions is usually carried out at from 350 to 650° C. for a period of from 0.5 to 6 hours.

Regeneration of the Dehydrogenation Catalyst

In the dehydrogenation of carbonyl compounds according to the present invention, small amounts of high-boiling, high molecular weight organic compounds or carbon are formed over time and these deposit on the catalyst surface and in the pores and eventually deactivate the catalyst.

Exhausted dehydrogenation catalysts are usually regenerated by flushing with inert gas, passing an oxygen-containing gas mixture through the catalysts, flushing with inert gas and subsequent activation by means of hydrogen, all at atmospheric pressure. In the process of U.S. Pat. No. 5,087,792, the catalyst is regenerated by flushing with inert gas, passing an oxygen-containing gas mixture through the catalyst, flushing with inert gas and subsequently passing an HCl/oxygen mixture through the catalyst to redisperse the active metal (palladium) on the support.

The regeneration process preferably comprises the following step (b):

(b) passing an oxygen-containing gas mixture comprising an inert gas through the catalyst at a pressure of from 0.5 to 20 bar and a space velocity of gas of from 1000 to 50 000 $h^{-1}$ for a period of from 0.25 to 24 hours while increasing the oxygen concentration either stepwise or continuously from an initial value of 0.01-1% by volume of $O_2$ to a final value of 10-25% by volume of $O_2$.

Before step (b) is carried out, the step (a) is usually carried out first:

(a) flushing with inert gas at a pressure of from 0.5 to 2.0 bar and a space velocity of gas of from 1000 to 50 000 $h^{-1}$.

If desired, the steps (c) and/or (d) are subsequently carried out:

(c) if desired, passing an oxygen-containing gas mixture comprising an inert gas through the catalyst at a pressure of from 0.5 to 20 bar and a space velocity of gas of from 10 to 500 $h^{-1}$ over a period of from 0.25 to 100 hours, with the oxygen concentration being from 10 to 25% by volume of $O_2$;

(d) if desired, repeatedly carrying out rapid opposite pressure changes by a factor of from 2 to 20 within the range from 0.5 to 20 bar.

It is usual to carry out step (e) after step (b), (c) or (d).

(e) flushing with an inert gas or stream

Preference is given to finally also carrying out the step (f).

(f) Activation of the catalyst by means of hydrogen.

It is usual to carry out at least one of the steps (c) and (d) and to carry out the entire regeneration process at from 300 to 800° C. Steps (b) and, if applicable, (c) are preferably carried out at above 500° C.

The dehydrogenation catalyst is preferably present in a dehydrogenation reactor. However, it can also be regenerated in a separate regeneration reactor.

In step (a), flushing with inert gas is preferably continued until the flushing gas no longer contains any appreciable traces of dehydrogenation product and hydrogen, i.e. traces which can no longer be detected by customary analytical methods, for example gas chromatography. At a pressure of from 0.5 to 2.0 bar and a space velocity of gas of from 1000 to 50 000 $h^{-1}$, this generally requires flushing for from 0.1 to 24 hours. The pressure is usually from 1 to 1.5 bar, and the space velocity of gas is preferably from 2000 to 20 000 $h^{-1}$. The flushing step is preferably carried out for a time of from 0.1 to 6 hours. Nitrogen is carried generally used as inert gas. In addition, water vapor can be present in the flushing gas in amounts of, for example, from 10 to 90% by volume.

In step (b), an oxygen-containing gas mixture is passed through the catalyst bed to burn off carbon deposits on the surface of the catalyst particles. The oxygen-containing gas mixture used is preferably diluted air which may further comprise water vapor in addition to an inert gas, for example in amounts of from 10 to 90% by volume. The oxygen content is gradually increased, generally from an initial concentration of 0.01-1% by volume, for example 0.1% by volume, to a final concentration of 10-25% by volume. If no water vapor is present in the oxygen-containing gas and air is employed, the final concentration is generally about 21% by volume of oxygen. It is important that the pressure employed is significantly above the pressure prevailing during the dehydrogenation. The pressure is preferably from 3 to 7 bar, for example from 4 to 6 bar. The treatment time is preferably from 0.5 to 12 hours, for example from 1 to 9 hours. A high space velocity of gas is generally employed. This is preferably from 2000 to 20 000 $h^{-1}$.

In step (c), an oxygen-containing gas mixture having a high proportion of oxygen is passed through the catalyst bed. Air is preferably used for this purpose. The oxygen-containing gas mixture can contain water vapor, for example in amounts of from 10 to 90% by volume. In this step, carbon deposited in the pores of the catalyst particles is burned off. This step is carried out at low space velocities of gas of generally from 10 to 500 $h^{-1}$, preferably from 20 to 100 $h^{-1}$. The pressure is not critical, and can be the same as or lower than the pressure in step (b). It is generally from 0.5 to 20 bar, preferably from 1 to 5 bar.

In step (d), the pressure is repeatedly altered rapidly in opposite directions, so that a pressure increase is followed by a pressure decrease at short time intervals. In this way, $CO_2$ formed in the pores can be effectively removed. The pressure is preferably altered from 2 to 20 times by a factor of from 2 to 5 within the range from 1 to 5 bar. For example, a total of 3 pressure increases and 3 pressure decreases from 1 to 5 and 5 to 1 bar are carried out. The total time for all pressure increase steps and pressure decrease steps is preferably from 0.1 to 1 hour. For the pressure to decrease quickly in the reactor, the space velocity of gas selected must not be too low and is generally from 100 to 50000 $h^{-1}$, preferably from 1000 to 20000 $h^{-1}$.

Step (c) and step (d) can be carried out alternatively; it is usual to carry out at least one of these steps. Step (d) is, in particular, carried out when step (c) has been carried out over a short period of, for example, from 0.25 to 5 hours. If step (c) is carried out over a longer period of, for example, from 20 to 100 hours, step (d) can be omitted.

In step (e), the catalyst is flushed with inert gas such as nitrogen or argon or steam, preferably for a period of from 1 minute to 1 hour. This is followed, in step (f), by the activation of the catalyst with hydrogen, as is known per se. It can be carried out using pure hydrogen or a hydrogen-containing gas which may contain an inert gas and/or water vapor, for example in amounts of from 10 to 90% by volume. The activation is preferably carried out at atmospheric pressure over a period of from 10 minutes to 2 hours.

In all steps (a) to (f), the temperature is generally from 300 to 800° C., preferably from 400 to 700° C. Steps (b) and (c) are preferably carried out at a temperature above 500° C.

Dehydrogenation

The gas-phase dehydrogenation of the carbonyl compound is carried out as a nonoxidative dehydrogenation. Here, the appropriate saturated carbonyl compound is at least partly converted into the alpha, beta-unsaturated carbonyl compound by dehydrogenation over the dehydrogenation-active catalyst in a dehydrogenation reactor, possibly also forming multiply unsaturated products. In addition, hydrogen and small amounts of low molecular weight by-products such as methane, ethane, ethene, propane and propene are obtained. Depending on the way in which the dehydrogenation is carried out, carbon oxides (CO, $CO_2$), water and nitrogen may also be present in the product gas mixture. In addition, unreacted starting material is generally also present in the product gas mixture.

As cyclic or acyclic carbonyl compounds, it is possible to dehydrogenate cyclic or acyclic aldehydes or ketones. Examples of acyclic aldehydes and ketones which can be dehydrogenated by the process of the present invention to form the corresponding alpha, beta-unsaturated compounds are propionaldehyde, butyraldehyde, valeraldehyde, isovaleraldehyde, butanone, 2-pentanone and 2-hexanone. The dehydrogenation occurs according to the following reaction scheme:

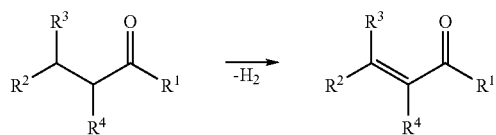

where $R^1$ is H or methyl, $R^2$ is H, methyl or ethyl and $R^3$ and $R^4$ are each, independently of one another, H, $C_1$-$C_4$-alkyl (methyl, ethyl, 1-propyl, 2-propyl, n-butyl, isobutyl, sec-butyl, tert-butyl) or substituted or unsubstituted phenyl or pyridyl.

Cyclic ketones which can be dehydrogenated by the process of the present invention are, for example, cyclopentanone, cyclohexanone and cycloheptanone. The dehydrogenation of the cyclic ketones occurs according to the reaction scheme:

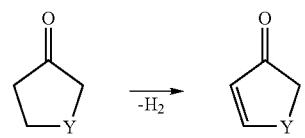

where Y is —$CH_2$—, —$CH_2CH_2$— or —$CH_2CH_2CH_2$—.

The nonoxidative catalytic dehydrogenation can be carried out with or without an oxygen-containing gas as additional feed gas stream.

A feature of the nonoxidative procedure compared to an oxidative mode of operation is the presence of hydrogen in the output gas. In oxidative dehydrogenation, no significant amounts of free hydrogen are formed.

The nonoxidative catalytic dehydrogenation can in principle be carried out in all reactor types and using all modes of operation known from the prior art. A quite comprehensive description of dehydrogenation processes suitable for the purposes of the present invention is given in "Catalytic® Studies Division, Oxidative Dehydrogenation and Alternative Dehydrogenation Processes" (Study Number 4192 OD, 1993, 430 Ferguson Drive, Mountain View, Calif., 94043-5272, USA).

A suitable type of reactor is a fixed-bed tube reactor or a shell-and-tube reactor. In these, the catalyst (dehydrogenation catalyst and, when using oxygen as additional feed gas stream, possibly a specific oxidation catalyst) is located as a fixed bed in a reaction tube or in a bundle of reaction tubes. The reaction tubes are usually heated indirectly by a gas, e.g. a hydrogen carbon such as methane, being burnt in the space surrounding the reaction tubes or by use of a heat transfer medium (salt bath, circulating gas, etc.). It is also possible to employ electric heating of the reaction tubes by means of heating sleeves. Customary internal diameters of the reaction tubes are from about 10 to 15 cm. A typical shell-and-tube reactor for dehydrogenation contains from about 10 to 10000 reaction tubes, preferably from about 10 to 200 reaction tubes. The temperature in the interior of the reaction tubes is usually in the range from 300 to 1200° C., preferably in the range from 400 to 600° C. The working pressure is usually in the range from 0.5 to 8 bar, frequently from 1 to 2 bar when using low steam dilution (as in the Linde process for propane dehydrogenation) or from 3 to 8 bar when using high steam dilution (as in the "steam active reforming process" (STAR process) for the dehydrogenation of propane or butane of Phillips Petroleum Co., cf. U.S. Pat. No. 4,902,849, U.S. Pat. No. 4,996,387 and U.S. Pat. No. 5,389,342). Typical space velocities over the catalyst (GHSV) are in the range from 500 to 2000 $h^{-1}$, based on hydrocarbon used. The catalyst geometry can, for example, be spherical or cylindrical (hollow or solid).

The nonoxidative catalytic dehydrogenation can also, as described in Chem. Eng. Sci. 1992 b, 47 (9-11) 2313, be carried out over a heterogeneous catalyst in a fluidized bed. It is advantageous to operate two fluidized beds in parallel, so that one of them is generally in the state of regeneration.

The working pressure is typically from 1 to 2 bar, and the dehydrogenation temperature is generally from 550 to 600° C. The heat required for the dehydrogenation is introduced into the reaction system by preheating the dehydrogenation catalyst to the reaction temperature. Mixing in an additional oxygen-containing feed gas stream (co-feed) makes it possible to omit the preheater, with the heat required being generated directly in the reactor system by combustion of hydrogen in the presence of oxygen. If appropriate, a hydrogen-containing co-feed can additionally be mixed in.

The nonoxidative catalytic dehydrogenation can be carried out with or without an oxygen-containing gas as co-feed in a tray reactor. This contains one or more catalyst beds arranged in succession. The number of catalyst beds can be from 1 to 20, advantageously from 1 to 6, preferably from 1 to 4 and in particular from 1 to 3. The reaction gas preferably flows radially or axially through the catalyst beds. Such a tray reactor is generally carried out using a fixed catalyst bed. In the simplest case, the fixed catalyst beds are arranged axially in a shaft furnace reactor or in the annular gaps of concentric cylindrical meshes. One shaft furnace reactor corresponds to one tray. Carrying out the dehydrogenation in a single shaft furnace reactor corresponds to a preferred embodiment in which an oxygen-containing cofeed can also be employed. In a further, preferred embodiment, the dehydrogenation is carried out in a tray reactor having 3 catalyst beds. In a mode of operation without an oxygen-containing gas as co-feed, the reaction gas mixture is subjected to intermediate heating, e.g. by passing it over heat-exchange surfaces heated by means of hot gases or by passing it through tubes heated by means of hot combustion gases, in the tray reactor on its way from one catalyst bed to the next catalyst bed.

In one embodiment of the process of the present invention, the nonoxidative catalytic dehydrogenation is carried out autothermally. For this purpose, oxygen is additionally mixed into the reaction gas mixture in at least one reaction zone and the hydrogen and/or hydrocarbon present in the reaction gas mixture is at least partially burnt, so that at least part of the necessary heat of dehydrogenation is generated directly in the reaction gas mixture in the reaction zone or zones.

In general, the amount of oxygen-containing gas added to the reaction gas mixture is chosen so that the heat necessary for the dehydrogenation is generated by combustion of hydrogen present in the reaction gas mixture and possibly of the carbonyl compounds present in the reaction gas mixture and/or of carbon present in the form of carbon deposits. In general, the total amount of oxygen introduced is, based on the total amount of carbonyl compounds, from 0.001 to 0.5 mol/mol, preferably from 0.005 to 0.2 mol/mol, particularly preferably from 0.05 to 0.2 mol/mol. Oxygen can be used as pure oxygen or as oxygen-containing gas comprising a mixture of oxygen and inert gases, for example in the form of air. The inert gases and the resulting combustion gases generally have an additional diluent effect and thus promote the heterogeneously catalyzed dehydrogenation.

The hydrogen burnt for generating heat is the hydrogen formed in the catalytic dehydrogenation plus, if desired, additional hydrogen added as hydrogen-containing gas to the reaction gas mixture. The amount of hydrogen present is preferably such that the molar ratio of $H_2/O_2$ in the reaction gas mixture directly after the introduction of oxygen is from 1 to 10 mol/mol, preferably from 2 to 5 mol/mol. In multistage reactors, this applies to each intermediate introduction of oxygen-containing and, if applicable, hydrogen-containing gas.

The combustion of hydrogen occurs catalytically. The dehydrogenation catalyst used generally also catalyzes the combustion of the carbonyl compound and of hydrogen with oxygen, so that in principle it is not necessary to use any specific oxidation catalyst different from this. In one embodiment, one or more oxidation catalysts which selectively catalyze the combustion of hydrogen by means of oxygen in the presence of the carbonyl compound are employed. In this way, the combustion of the carbonyl compound by means of oxygen to form CO, $CO_2$ and water occurs to only a subordinate extent. The dehydrogenation catalyst and the oxidation catalyst are preferably present in different reaction zones.

When the reaction is carried out in a plurality of stages, the oxidation catalyst can be present in only one reaction zone, in a plurality of reaction zones or in all reaction zones.

The catalyst which selectively catalyzes the oxidation of hydrogen is preferably located in those places where the prevailing oxygen partial pressures are higher than at other places in the reactor, in particular in the vicinity of the feed point for the oxygen-containing gas. Oxygen-containing gas and/or hydrogen-containing gas can be fed in at one or more points on the reactor.

In one embodiment of the process of the present invention, intermediate introduction of oxygen-containing gas and of hydrogen-containing gas is carried out upstream of each tray of a tray reactor. In a further embodiment of the process of the present invention, oxygen-containing gas and hydrogen-containing gas are fed in upstream of each tray apart from the first tray. In one embodiment, a bed of a specific oxidation catalyst is present downstream of each point of introduction, followed by a bed of the dehydrogenation catalyst. In a further embodiment, no specific oxidation catalyst is present. The dehydrogenation temperature is generally from 400 to 1100° C., and the pressure in the last catalyst bed of the tray reactor is generally from 0.2 to 5 bar, preferably from 1 to 3 bar. The space velocity (GHSV) is generally from 500 to 2000 $h^{-1}$, and in high-load operation up to 100 000 $h^{-1}$, preferably from 4000 to 16000 $h^{-1}$.

A preferred catalyst which selectively catalyzes the combustion of hydrogen comprises oxides and/or phosphates selected from the group consisting of the oxides and/or phosphates of germanium, tin, lead, arsenic, antimony or bismuth. A further preferred catalyst which catalyzes the combustion of hydrogen comprises a noble metals of transition groups VIII and/or I.

Work-up of the Dehydrogenation Output

The work-up of the dehydrogenation output can be carried out continuously or batchwise.

The output from the dehydrogenation reaction consists essentially of the alpha, beta-unsaturated carbonyl compound, unreacted starting compound, water, hydrogen, CO, $CO_2$ and low-boiling hydrocarbons such as methane, ethene, ethane, propene and propane. Low-boiling constituents of the reactor output can be separated off in a condenser, giving a mixture of water, product end starting material as condensate. Owing to the high polarity of the starting and product carbonyl compounds, phase separation into organic and aqueous phases is frequently poor or does not occur at all. In this case, the work-up can include extraction of the aqueous condensate with an organic extractant. Preference is given to using an extractant which has either a significantly higher or significantly lower boiling point than starting material and product. The extractant is subsequently recovered in a distillation. The starting material/product mixture which remains is subsequently fractionated in a further distillation. The recovered starting material is preferably returned to the dehydrogenation. If azeotropes between water and the starting material and/or product occur, the extractant is preferably selected so that the water remaining in the aqueous phase is at the same time carried out when the extractant is distilled off. As an alternative, water can also be separated off by azeotropic distillation using a suitable entrainer such as cyclohexane in place of an extraction.

Figure 1:
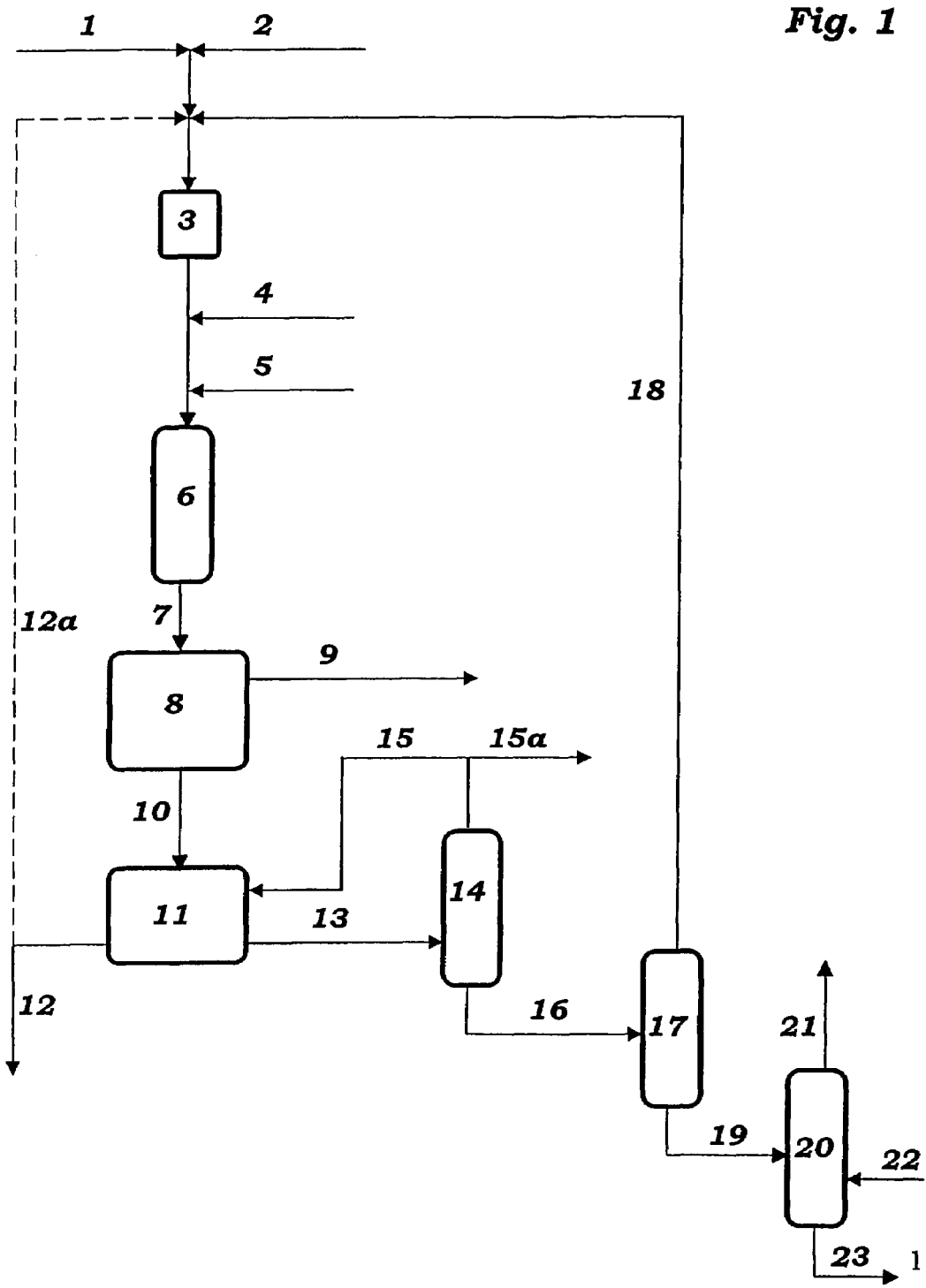
FIG. 1 details the dehydrogenation of cyclopentanone to 2-cyclopenten-1-one.

The work-up can be carried out as shown by way of example in the figure for the dehydrogenation of cyclopentanone to 2-cyclopenten-1-one. Cyclopentanone (1) and a water/steam mixture (2) are fed into the vaporizer (3) and vaporized together. Hydrogen (4) and optionally oxygen or an oxygen-containing gas (5). are fed into the gaseous cyclopentanone/water vapor mixture and the gas mixture is fed into the dehydrogenation reactor (6). The reactor output (7) consists essentially of the dehydrogenation product 2-cyclopenten-1-one, unreacted cyclopentanone, water vapor, hydrogen, CO, $CO_2$ and low-boiling hydrocarbons such as methane. In the condenser (8), low boilers (9) such as hydrogen, CO, $CO_2$ and methane are separated off. The condensate (10) consists essentially of water, 2-cyclopenten-1-one and cyclopentanone. In a subsequent extraction stage (11), the organic constituents of the condensate (10) are extracted by means of an organic extractant (15). Suitable organic extractants are, for example, ethyl acetate, methyl tert-butyl ether and dichloromethane. The aqueous phase leaving the extractant stage (11) can be at least partly returned as substream (12a) to the dehydrogenation. The organic phase (13) leaving the extraction stage, which consists essentially of 2-cyclopenten-1-one, cyclopentanone and organic extractant, is passed to the distillation column (14) in which the organic extractant is taken off at the top, for example at a pressure of 150 mbar, and thus recovered. To avoid the accumulation of by-products, a substream (15a) (purge stream) of the recovered extractant is bled off from the main stream (15). The bottom offtake stream (16) consisting essentially of cyclopentanone and 2-cyclopenten-1-one is separated in a further distillation column (17), preferably under subatmospheric pressure, for example at 70 mbar, into cyclopentanone 18 as overhead product and 2-cyclopenten-1-one (19) as bottom product. The cyclopentanone 18 is recirculated to the dehydrogenation. The crude product (19) is further purified by distillation in a downstream pure distillation column (20), giving the pure product as overhead offtake stream (21). The pure distillation column (20) is preferably operated at subatmospheric pressure, for example 30 mbar. Bottoms fluidizers (22), for example propylene carbonate or fatty alcohol ethoxylates, are added. High-boiling impurities are removed together with the bottoms fluidizer as bottom offtake stream (23) (purge stream).

The invention is illustrated by the examples below.

EXAMPLES

Example 1

Preparation of the Dehydrogenation Catalyst

A solution of 11.992 g of $SnCl_2.2H_2O$ and 7.888 g of $H_2PtCl_6.6H_2O$ in 5950 ml of ethanol was poured over 1000 g of a crushed $ZrO_2.SiO_2$ mixed oxide from Norton (sieve fraction: 1.6 to 2 mm).

The supernatant ethanol was taken off on a rotary evaporator. The solid was subsequently dried at 100° C. for 15 hours and calcined at 560° C. for 3 hours. A solution of 7.68 g of $CsNO_3$, 13.54 g of $KNO_3$ and 98.329 g of $La(NO_3)_3.6H_2O$ in 23 ml of $H_2O$ was then poured over the resulting catalyst. The supernatant water was taken off on a rotary evaporator. The solid was then dried at 100° C. for 15 hours and calcined at 560° C. for 3 hours.

The catalyst had a BET surface area of 85 $m^2/g$. Mercury porosimetry measurements indicated a pore volume of 0.29 ml/g.

Example 2

Dehydrogenation of Cyclopentanone to 2-cyclopentenone

Cyclopentanone and water are vaporized together by means of a vaporizer and dehydrogenated over the catalyst from Example 1 in a continuous process at 500° C. in a tube reactor. The mass ratio of the feeds water vapor:cyclopentanone is 1:1. The feed mixture is passed over the catalyst at an LHSV of 1.25/h. The LHSV is defined as cyclopentanone flow (defined as liquid volume flow under standard conditions) per unit volume of catalyst bed.

The reactor output is liquefied at 0° C. in a condenser and separated off from uncondensed gaseous constituents. The liquefied reactor output, which contains about 50% of water, is extracted with ethyl acetate. After separation of the two phases, the organic phase, which consists essentially of the extractant, cyclopentanone and cyclopentenone, is subjected to a fractional distillation.

The extractant (ethyl acetate) is firstly distilled off at the top at 150 mbar and 40° C. The high-boiling fraction taken off at the bottom is admixed with bottoms fluidizer. In the subsequent distillation stages, once again under reduced pressure, cyclopentanone is firstly separated off from these bottoms at the top at 70 mbar and 60° C. and 2-cyclopenten-1-one is finally separated off at the top at 30 mbar and 60° C.

The cyclopentenone obtained has a purity of >99.5%. The recovered cyclopentanone is reused for the dehydrogenation. The extractant is returned to the extraction.

In an 8 hour test run, an average conversion of 18%, dropping from about 24% after 1 hour to about 8% after 8 hours, was achieved at an average selectivity for the formation of 2-cyclopenten-1-one of 85%. By-products formed apart from organic deposits on the catalyst were virtually exclusively gaseous compounds such as methane, ethylene, propylene and carbon oxides.

The catalyst is regenerated at regular intervals.

Example 3

The example was carried out in a manner analogous to Example 2, but at an LHSV of 0.4 $h^{-1}$ and a proportion of water vapor of 50% by weight, based on cyclopentanone. The outputs were collected and analyzed after 8 hours. A conversion of 24.8% was found.

We claim:

1. A process for preparing alpha, beta-unsaturated acyclic or cyclic carbonyl compounds by dehydrogenation of the corresponding saturated carbonyl compounds in the gas phase over a heterogeneous dehydrogenation catalyst comprising platinum and/or palladium and tin on an oxidic support.

2. A process as claimed in claim 1, wherein the oxidic support is selected from the group consisting of zirconium dioxide, aluminum oxide, silicon dioxide, titanium dioxide, magnesium oxide, lanthanum oxide and cerium oxide.

3. A process as claimed in claim 1, wherein the dehydrogenation catalyst comprises zirconium dioxide and/or silicon dioxide.

4. A process as claimed in claim 1, wherein the dehydrogenation catalyst further comprises at least one element of main group I or II and at least one element of transition group III including the lanthanides and actinides.

5. A process as claimed in claim 1, wherein the dehydrogenation catalyst comprises cesium and/or potassium.

6. A process as claimed in claim 1, wherein the dehydrogenation catalyst comprises lanthanum and/or cerium.

7. A process as claimed in claim 1, wherein the dehydrogenation is carried out in the presence of molecular oxygen under autothermal conditions.

8. A process as claimed in claim 1 in which a regenerated dehydrogenation catalyst is used and the regeneration comprises at least the following step:

passing an oxygen-containing gas mixture comprising an inert gas through the catalyst bed at a pressure of from 2 to 20 bar and a space velocity of gas of from 1000 to 50 000 h$^1$ for a period of from 0.25 to 24 hours while increasing the oxygen concentration either stepwise or continuously from an initial value of 0.01-1% by volume of O$_2$ to a final value of 10-25% by volume of O$_2$.

9. A process as claimed in claim 8, wherein the regeneration of the dehydrogenation catalyst comprises the steps (a), (b) and (e) and, if desired, (c), (d) and (f):

(a) flushing with inert gas at a pressure of from 0.5 to 2.0 bar and a space velocity of gas of from 1000 to 50 000 h$^{-1}$;

(b) passing an oxygen-containing gas mixture comprising an inert gas through the catalyst bed at a pressure of from 2 to 20 bar and a space velocity of gas of from 1000 to 50 000 h$^{-1}$ for a period of from 0.25 to 24 hours while increasing the oxygen concentration either stepwise or continuously from an initial value of 0.01-1% by volume of O$_2$ to a final value of 10-25% by volume of O$_2$;

(c) if desired, passing an oxygen-containing gas mixture comprising an inert gas through the catalyst at a pressure of from 0.5 to 20 bar and a space velocity of gas of from 10 to 500 h$^{-1}$ over a period of from 0.25 to 100 hours, with the oxygen concentration being from 10 to 25% by volume of O$_2$;

(d) if desired, repeatedly carrying out rapid opposite pressure changes by a factor of from 2 to 20 within the range from 0.5 to 20 bar;

(e) flushing with an inert gas;

(f) activation of the catalyst by means of hydrogen;

where at least one of the steps (c) or (d) is carried out and the entire regeneration process is carried out at from 300 to 800° C.

10. A process as claimed in claim 8, wherein steps (b) and, if applicable, (c) are carried out at >500° C.

11. A process as claimed in claim 1, wherein the cyclic or acyclic carbonyl compounds are cyclic or acyclic aldehydes or ketones.

12. A process as claimed in claim 11, wherein an acyclic aldehyde or ketone selected from the group consisting of propionaldehyde, butyraldehyde, valeraldehyde, isovaleraldehyde, butanone, 2-pentanone and 2-hexanone is dehydrogenated.

13. A process as claimed in claim 11, wherein a cyclic ketone selected from the group consisting of cyclopentanone, cyclohexanone and cycloheptanone is dehydrogenated.

14. A process as claimed in claim 2, wherein the dehydrogenation catalyst comprises zirconium dioxide and/or silicon dioxide.

15. A process as claimed in claim 2, wherein the dehydrogenation catalyst further comprises at least one element of main group I or II and at least one element of transition group III including the lanthanides and actinides.

16. A process as claimed in claim 3, wherein the dehydrogenation catalyst further comprises at least one element of main group I or II and at least one element of transition group III including the lanthanides and actinides.

17. A process as claimed in claim 2, wherein the dehydrogenation catalyst comprises cesium and/or potassium.

18. A process as claimed in claim 3, wherein the dehydrogenation catalyst comprises cesium and/or potassium.

19. A process as claimed in claim 4, wherein the dehydrogenation catalyst comprises cesium and/or potassium.

20. A process as claimed in claim 5, wherein the dehydrogenation catalyst comprises lanthanum and/or cerium.

* * * * *